(12) United States Patent
Alt

(10) Patent No.: US 6,613,083 B2
(45) Date of Patent: Sep. 2, 2003

(54) STENT DEVICE AND METHOD

(76) Inventor: Eckhard Alt, Eichendorffstr. 52, Otttobrunn (DE), 85521

( * ) Notice: Subject to any disclaimer, the term of this patent is extended or adjusted under 35 U.S.C. 154(b) by 0 days.

(21) Appl. No.: 09/847,626

(22) Filed: May 2, 2001

(65) Prior Publication Data

US 2002/0165607 A1 Nov. 7, 2002

(51) Int. Cl.$^7$ ................................................. A61F 2/06
(52) U.S. Cl. ..................................................... 623/1.42
(58) Field of Search ................................ 623/1.38, 1.39, 623/1.41, 1.42, 1.43, 1.44, 1.45, 1.46, 1.47, 1.48, 23.7–23.76

(56) References Cited

U.S. PATENT DOCUMENTS 6,153,252 A * 11/2000 Hossainy et al. ............ 427/2.3

* cited by examiner

Primary Examiner—Corrine McDermott
Assistant Examiner—Alvin Stewart

(57) ABSTRACT

A stent for delivering a therapeutic dose of the immnuosupressant tacrolimus is disclosed.

9 Claims, 1 Drawing Sheet

STENT DEVICE AND METHOD

FIELD OF THE INVENTION

The invention relates generally to stents and more particularly to a drug delivery endovascular stent which delivers a specific immunosuppressant drug to the stent treatment site.

BACKGROUND OF THE INVENTION

Stents are a widely used adjunct to coronary artery interventions. After an angioplasty or other intervention, a stent may be introduced to the treatment site to support the wall of the artery.

The principle problem with stent usage is a re-closure process called restenosis. The problem of restenosis is widely recognized. It appears from research that the mechanisms for restenosis after a balloon procedure differs in detail from the healing processes associated with stent placement.

The biological reactions associated with the use stents causes a cascade of cellular growth and proliferation. The mechanical action of the stent against the artery wall (spring back) and the introduction of the foreign substance into the body results in an inflammatory response which gives rise to signaling molecules called cytokines which mediate a variety of biologic processes. Although the magnitude and course of the inflammatory response varies widely among patients, the body isolates the foreign material of the stent by encapsulating it with cell growth. Consequently a pseudo intima will be produced on the surface of the stent. In general the propagation of a smooth muscle tissue pseudo intima is desirable, however in some patients the proliferation of smooth muscle cells and their conversion to secretory muscle cells results in re-closure of the vessel within a short period of time. Although this is a normal response to the insertion of a foreign body, given the location of the stent it results in severe clinical problems. Other short term complications exist as well including acute thrombosis. The delivery of anti platelet drugs and other thrombolytic drugs have been proposed to treat this near term type of reclosure.

Several efforts have been made to prevent or delay the longer term restenosis process. One approach has been to implant radioactive stents where the local emission of beta radiation inhibits hyperplasia. Although intracoronary radiation is effective at preventing restenosis this grossly interferes with the healing process previously described and can lead to secondary complications such as edge restenosis and late thrombosis. One example of this stent technology is known from U.S. Pat. No. 5,871,437 to Alt. This reference teaches the use of multiple coating on the stent substrate. One coating carries a beta emitter while other coatings deliver a anticoagulation drug.

Another approach to the treatment of acute thrombosis in stent treatments is discussed in U.S. Pat. No. 5,788,979 to Alt et al. The stent according to this invention uses a biodegradable coating to release a controlled amount of a therapeutic agent such as an a anti-coagulant, antithrombogenic, or antistenotic drug. The biodegradable coating provides a local release of drug which improves the bio-compatibility of the stent and reduces inflammation and the hyperplasia processes. The objective or these different methods is to interfere with and control the proliferation of the smooth muscle cells.

Although the various coated stents improve the restenosis rates for some patients, a fully bio-compatible stent remains an elusive problem as the factors of local thrombus formation, vessel injury and inflammation interact in complex and individually variable ways. For these reasons re-occlusion and restenosis problems are difficult to manage in a clinical setting. Restenosis remains a significant risk for patients.

SUMMARY

In contrast to the prior art, the stent of the present invention delivers an effective dose of the immunosuppressant drug tacrolimus to the stent treatment site. The tacrolimus is delivered at a rate and in a concentration that both encourages proliferation of smooth muscle cells and limits conversion of such cells to the secretory type muscle cells. This method and approach differs from the prior art cytostatic techniques where Taxol and related drugs are used in an overall strategy to interfere with and delay the healing response.

In accord with the method and device of the of the present invention a stent delivers tacrolimus to the cells proliferating on the surface of the stent. The stent forms a primary structure and the coating is a secondary process. In general it is preferred to use a polymer coat but surface modification of the stent itself to create a drug delivery surface is possible though not preferred.

The preferred device delivers drug by elution from a polymer matrix applied as a coating to the stent. The polymer matrix may be permanent and non biodegradable or it may be biodegradable. An example of a suitable biodegradable material is polylactic acid (PLA). Examples of more permanent matrix materials includes; polyethylene; vinyl acetate and medical polyurethanes and silicone rubber. Other biodegradable and non-biodegradable materials are contemplated within the scope of the inventions well. The primary requirement is the formation of a biocompatible matrix to allow elution of the tacrolimus.

The localized and selective delivery of the tacrolimus and tacrolimus containing compounds encourages endothelization of the stent with smooth muscle cells and other endothelial cells and discourages the proliferation and conversion of such cells to secretory smooth muscle cell types.

The beneficial effect of tacrolimus and its analogues is unknown in this context and the drug is not indicated for or labeled for use in cardiovascular interventions.

Although arterial endovascular and specifically coronary interventions are an important application for this invention it should be recognized that other biomedical devices and device locations, sizes and drug concentrations are contemplated within the scope of the invention. It must also be recognized that additional features and structures may be added to the invention without departing from the scope of the invention.

BRIEF DESCRIPTION OF THE DRAWINGS

Throughout the figures of the drawing like reference numerals represent identical structure, wherein.

DETAILED DESCRIPTION

Figure 1:
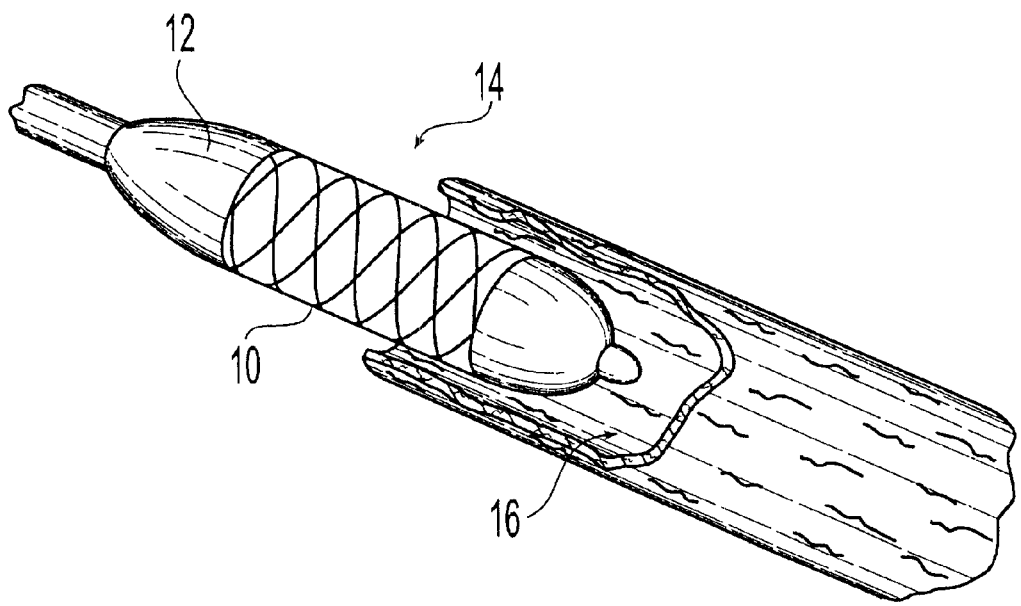
FIG. 1 shows a stent being delivered to a treatment site.

FIG. 1 shows a stent 10 which has been crimped onto an angioplasty balloon 12. The assembly 14 is being delivered to a treatment site 16 in an arterial vessel 16. In a typical intervention the stent 10 will be made of a metal mesh and this primary structure will be mechanically deformed onto a balloon after it has been coated with the drug. After insertion into the treatment site 16 the stent 10 will be deployed by expanding it into the tissues at the treatment site. The secondary coating on the surface of the primary structure will be in contact with the tissue at the treatment site and the stent will be exposed to a continuous flow of blood at the site.

Figure 2:
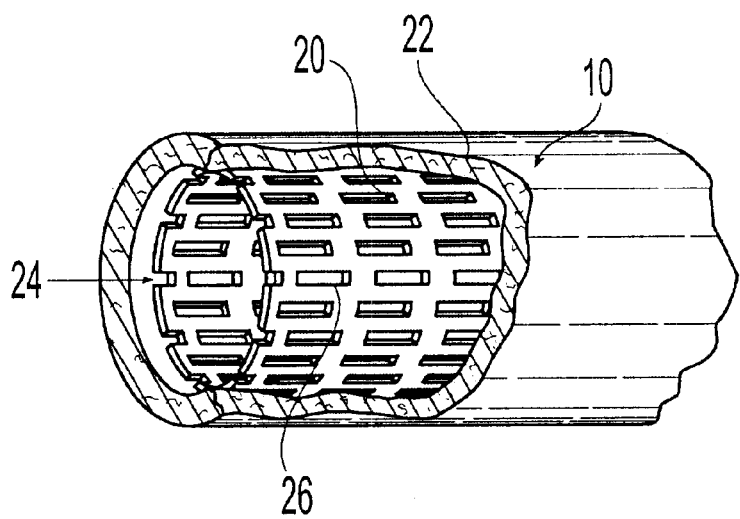
FIG. 2 shows a stent with the preferred coating applied.

FIG. 2 shows a partial cross section of a segment of the stent. 10 The metal substrate 20 provides the mechanical characteristics for the stent and is the primary structure as is well known in this art. As seen in the figure the stent 10 is a hollow tube having open ends typified by open end 24 and a side wall substrate 20 with multiple apertures typified by aperture 26.

The secondary coating 22 is preferable a biodegradable polymer such as PLA carrying a concentration of the drug tacrolimus. The preferred approach is to dissolve the Tacrolimus in the selected polymer and dip coat the stent. In this preferred process the tacrolimus is uniformly distributed in the coating. It is important to note that other approaches may be adopted as well. For example the surface of the stent may be modified to exhibit porosity. This matrix may be considered a secondary coating and it may be loaded or filled with tacrolimus or a tacrolimus contains compound in another operation.

EXAMPLE

The following protocol details an illustrative proposed test stent according to the invention.

Approximately 40 mg of R203, a polylactic acid of a molecular weight of 30 kDa, is dissolved in 0.6 ml chloroform together with 10 mg of tacrolimus. The resulting solution yields a weight-related content of 20% of tacrolimus in the coating.

The stents are dip-coated at reduced temperate in several steps in order to apply an approximately 10 $\mu$m thick coating on the stent surface.

Next the stents are crimped on a balloon. When used in a patient the stent will be expanded into a vessels of a patient to a maximum diameter of 4.5 mm. The expansion of the stent places the polymer matrix which is acting a secondary coating in contact with the tissues at the site of stent placement. Stents proposed for use are conventional in design and are commercially available from InFlow Dynamics (InFlow Starflex Stent Design).

Expected Mechanism of Operation and Interaction with the Body

Tacrolimus was discovered in 1984 in the culture medium of a bacterium that was detected in the soil in Japan. The bacterium was called *Streptomyces tsukubaensis*, and has shown to have interesting properties. Initially it was assumed to belong to the group of the macrolide antibiotics such as erythromycin.

Tacrolimus has a molecular weight of 822 Da, it is a white crystalline powder and it has both a lipophilic and strong hydrophobic behavior which are exploited in the invention. It is soluble in chloroform, ethylacetate acetone, and ethanol, and is practically insoluble in water. This drug is available from Fujisawa Inc. of Japan.

The approved indications for the drug vary between countries. In the US, tacrolimus is currently approved for the use in the prophylaxis of organ rejection in patients receiving liver or kidney transplant. In UK and Canada, tacrolimus is indicated for primary therapy and rescue therapy for graft rejection resistant to conventional immunosuppressive regimen and several European countries have approved the drug for heart transplantation.

The applicant has observed in restenosis that the infiltration of lymphocytes, macrophages, and plasmacells end in matrix production of smooth muscle cells.

It is believed that the production of T-helper cells and the production of cytokines are an important mechanism in the immunoresponse to a foreign body. If the stent surface is recognized as a foreign body by the CD4 identifiable helper cells ($T_{H1}$, $T_{H2}$), this induces a T-cell proliferation. The helper cells produce various cytokines such as interleukine 2, interferon $\gamma$ (IFN$\gamma$) that cause an activation of killer and cytotoxic T-cells as well as polynuclear granulocytes and mastcells. The mastcells themselves produce interleukine 1 and 2, which also enhance the proliferation of the T-cells. This response results in cellular cytotoxicity and antibody creation.

Interferon $\gamma$ enhances the expression of intercellular adhesion molecules (ICAM1), that increases the adhesion of T-cells to the endothelial cells. This also effects a local thrombus formation on the endothelial cells and increases the endothelial permeability.

It appears the interleukine 8 especially promotes the adhesion and transepithelial migration of T-cells into the neointimal build-up. In transplant rejections, an increase in interleukine 8 production precedes the rejection of the organ by several days. In summary, the rejection of a foreign body is carried forward primarily by T lymphocytes, monocytes, macrophages, and killercells that are upregulated by a wide variety of cytokines such as interleukine 2, 4, 5, 6, 8, and 10, interferon $\gamma$, and TNF$\gamma$.

When a T-cell recognizes the antigenic foreign surface then, upon activation, phospholipases (PLC) induce the generation of inositol-triphosphate ($IP_3$), a primarily calcium dependent signal transduction. Calcineurin diphosphorylizes the nuclear factor of activated lymphocytes in the cytoplasma (NF-ATC) and induces its translocation into the nucleus (NF-AT).

At the nucleus, this complex induces the transcription of interleukines 2, 3, 4, 5, and 8 genes as well as the transcription of TGF$\beta$ and of the tumornecrosis factor $\alpha$. The transcription of the specific cytokine genes into mRNA results in the production of the respective cytokines by the T-cell.

Tacrolimus has a specific binding site in the cytoplasma. This binding protein is called FKBP-12. The binding of tacrolimus to this receptor binds to the calcineurine and inhibits the calcium dependent signal transduction. By this way, it inhibits the translocation of the cytoplasmatic NF-ATC from the cytoplasma into the nucleus and thereby the expression of the above mentioned cytokines.

TGF$\beta$ is not only released by T lymphocytes, but also by activated endothelial cells. Endothelial cells have a wide range of purposes and action. Aside from the production of the nitrogen monoxide NO, that inhibits vascular smooth muscle cell proliferation, endothelial cells are capable upon stimulation to produce also growth factors such as insuline-like growth factor (IGF1), basic fibroblast growth factor (bFGF), interleukine 6, and especially transforming growth factor $\beta$. In addition, if upon stimulation of interleukine 4, tumornecrosis factor $\alpha$, and interferon $\gamma$ the expression of ICAM-1 increases, the endothelial layer is more permeable to the cytokines and allows them to penetrate through the endothelial layer.

TGF$\beta$ has the capability to transit smooth muscle cells from their contractile state into its proliferative form. In this form, the cells are very secretory and produce a wide variety of intercellular matrix, among them various collagens and proteoglykanes.

Applicant believes that the primary action of tacrolimus is that it acts both as a suppressor of the inflammatory reaction against the foreign stent body and as a competitive inhibitor at the FKBP-12 receptor of smooth muscle cells and prevents them to enter the secretory state. Applicant believes that the important factor to be addressed in stent coatings is the immunoresponse toward the foreign body of the stent.

In a recent study, the different inhibitory effects of immunosuppressive drugs on human and rat aortic smooth muscle cells and endothelial cell proliferation were studied. This trial revealed that tacrolimus very modest antiproliferative properties on vascular cells. This means that the normal wound healing response is not compromised, but the transition to the secretory smooth muscle cell type that is responsible for the restenosis build up is practically totally inhibited. This is the major difference between this and other immunosuppressive drugs that inhibit all normal wound healing responses.

Also methylprednisolone showed a gradual inhibition over a broad concentration interval in rat and human smooth muscle cells, but not of human endothelial cells.

Dosage

Since only a limited amount of drug can be coated onto the surface of a stent, the most potent drug should be used. In clinical practice, the dosage for tacrolimus normally is a range of 0.04–0.06 mg/kg/day, if given intravenously. This means about 4 mg per day for a 75 kg patient are applied, a level in the whole blood of 10–20 ng/ml is the primary goal.

The dosages of cyclosporine and of mycophenolic acid which are used for immunosurpression are 10 to 100-fold higher in order to achieve similar effect.

A second aspect makes tacrolimus highly superior over cyclosporine, is its dual action on the cytokine inhibition. While cyclosporine also inhibits the cytokine release from T-cells, it has not the competitive inhibitory effect of TGFβ in smooth muscle cells, which is according to the hypothesis of this study the major action of arteriosclerosis and restenosis associated with the foreign body implant of a stent.

Tacrolimus is a lipophilic substance which is practically insoluble in water. Therefore, its distribution in the blood is primarily intracellular in red blood cells, in the plasma it is bound to α-1 sour glycoproteins and albumins. This means, that if coated to a stent the concentration in the cells will be high, while the solution into plasma is low, resulting in a high local concentration.

Previous studies with PLA-coating have shown that a thickness of 10 μm of PLA on the stent surface is favorable. This means, that on a 16 mm long stent on average 500 μg of carrier are applied by means described previously. In order not to compromise the physical characteristics of such a stent coating, a maximum of 20% of drug can be incorporated into the carrier. This means, that roughly 100 μg tacrolimus to a stent can be applied. Assuming a release over more than 10 days, the total dosage released is less than 1/1000 of the dosage given intravenously. Assuming that the majority is not released into the blood and that tacrolimus has a halflife of 12 hours, the systemic dosage released from the stent coating is $10^{5-6}$ below that what is needed for a systemic action.

Assuming a release similar to other drugs incorporated into the PLA carrier a minimum intracellular level of tacrolimus in the therapeutic range of 5–20 ng/ml tissue can be achieved in the adjacent wall.

Bio-resorbable Coating

There is a complex reaction between the body and a material like PLA. The kinetics of this reaction governs in part the release of the tacrolimus. To test the elution it is proposed to fill 10 vials with 3 stents each are and to incubate them at 37° C. A magnetic stirrer induces a constant flow of the lipophilic solution into which the stents are immersed. Aliquots are taken at different time intervals, frozen, and subjected to high pressure liquid chromatography (HPLC) in order to detect the release level of tacrolimus and dexamethasone. Enzyme immunoassay systems that can detect down to a minimum of 0.5 ng/ml tacrolimus in the solution are to be used. Samples are taken at 1 hour, 12 hours, 24 hours, 48 hours, 6, 12, 24, and 30 days and then subjected to the assay.

Every time aliquots are taken (10 μl), the same amount of solution is added in order to keep the concentration the same.

The degradation of the PLA matrix has been tested in the past and described. In principle, at 37° C. also a magnetic stirrer tests the weight loss of stents in a saline solution. PLA degrades by hydrolysis to lactic acid. Previous calculations have shown, that if the entire amount of polymere was immediately degraded, this would result in roughly 5 pmol of lactic acid, that would be diluted in an average blood volume of 7 l. This would respond to a burden of lactic acid of about $10^{-6}$ μmol/ml lactate, well below the level of lactate present in blood after strenuous exercise (2–4 μmol/l).

Non Bio-Resorbable Coating

Non digestible coatings can be used as well. In addition to surface modification of the metal of the stent several polymer coats are contemplated. In this embodiment the polymer coating acts as an alternative to the PLA and the pharmo-kinetics related to dose administration must be tailored to provide a therapeutic dose based on the composition of the polymer. It is expected that the drug will be released though a diffusion process over a number of days. The polymer matrix should be tailored to achieve a therapeutic release. It is expected that polyurethanes and polyethylene and similar plastics will be useful in this application.

What is claimed is:

1. A method of preventing restenosis following stent implantation, said method comprising performing localized and selective delivery of tacrolimus or its analogues at the site of the stent implantation, at a rate and concentration that allows normal wound healing but limits inflammatory response that results in the formation of restenosis.

2. The method of claim 1, including controlling said rate and concentration to prevent the shift of smooth muscle cells at the stent implantation site from a contractile to a matrix producing secretory cell type.

3. A body-implantable stent, comprising:
   an open-ended tubular structure with apertures in its sidewall that allow the stein to be radially expanded so as to engage tissue and remain in place at the inner surface of the wall of an artery, vessel, duct, or tract of a patient's body at a selected stent implantation site; and
   a surface coating of tacrolimus or an analogue thereof on said structure, said coating being tailored and adapted to achieve a localized concentration within the artery, vessel, duct, or tract at the stent implantation site to allow normal wound healing to take place, while concurrently limiting an inflammatory response that would result in restenosis, at said site.

4. The body-implantable stent of claim 3, wherein
said localized concentration is predetermined to produce a rate of delivery of tacrolimus or said analogue thereof at the stent implantation site to prevent a transformation of smooth muscle cells at said site from a contractile cell type to a matrix producing secretory cell type.

5. A vascular or endoluminal stent having an outer surface adapted to reside firmly against the inner surface of the wall of an artery, vessel, duct, or tract of a patient's body at the site of deployment of the stent to maintain an open lumen for perfusion at said site; said stent having a coating of tacrolimus or an analogue thereof in a polymer matrix on said outer surface tailored and adapted for therapeutic release of tacrolimus or said analogue thereof from the stent coating at the deployment site in a concentration and at a rate adequate to achieve, concurrently, (i) an immuno-suppressive response sufficient to inhibit rejection of the stent by the body, (ii) an anti-inflammatory response sufficient to inhibit steriosis at said site, and (iii) an anti-proliferative effect insufficient to compromise the body's natural wound healing response at said site.

6. An implantable stein comprising:
a biocompatible surface coating on an outer surface of said stent, said coating including a predetermined concentration of tacrolimus or an analogue thereof for therapeutic release from said coating, when the stent is deployed for retention against the wall of a vessel, duct, or tract of a patients body at a selected stent implantation site where an open lumen is to be maintained, said therapeutic release being substantially localized at said site at a rate which is sufficient to produce an immuno-suppressive response that resists the body's natural tendency toward rejection of the stent and an anti-inflammatory response that inhibits restenosis at said site, while being insufficient to produce an anti-proliferative effect that prevents a natural wound healing response to presence of the stent at said site.

7. A method of achieving a relatively strong immuno-suppressive response of a patient's body to implantation of a stent in an artery, vessel, duct, or tract of the body so as to inhibit the body's natural defense toward rejecting the stent as a foreign object, without substantial proliferative response of the body to trauma created by presence of the stent so as to avoid compromising the body's natural wound healing response at the stent implant site, while producing an anti-inflammatory response that resists development of restenosis at said site, said method comprising administering an effective dose of tacrolimus locally at the stent implant site for delivery of the tacrolimus to said site at a rate and in a concentration that encourages proliferation of smooth muscle cells of a contractile type and limits conversion of such cells to a secretory type.

8. A device for maintaining an open lumen at a site in the cardiovascular system at which the device is implanted, comprising incorporating a dose of tacrolimus in a coating on said device adapted to reside against the wall of the vessel at the implant site to deliver the tacrolimus locally at a rate and in a concentration that allows normal wound healing but limits inflammatory response that results in the formation of restenosis.

9. The device of claim 8, wherein said rate and concentration of tacrolimus delivered to said site is selected to prevent smooth muscle cells proliferating at the site from undergoing transformation from a contractile cell type to a secretory cell type.

* * * * *

UNITED STATES PATENT AND TRADEMARK OFFICE
CERTIFICATE OF CORRECTION

PATENT NO. : 6,613,083 B2
APPLICATION NO. : 09/847626
DATED : September 2, 2003
INVENTOR(S) : Eckhard Alt Page 1 of 1

It is certified that error appears in the above-identified patent and that said Letters Patent is hereby corrected as shown below:

In claim 3, col. 6, line 58, "stein" should be --stent--.
In claim 5, col. 7, line 20, "steriosis" should be --stenosis--.
In claim 6, col. 7, line 24, "stein" should be --stent--.

Signed and Sealed this

Thirty-first Day of July, 2007

JON W. DUDAS
*Director of the United States Patent and Trademark Office*